(12) United States Patent
Tanoue et al.

(10) Patent No.: US 10,791,995 B2
(45) Date of Patent: Oct. 6, 2020

(54) MAGNETIC RESONANCE IMAGING APPARATUS

(71) Applicant: TOSHIBA MEDICAL SYSTEMS CORPORATION, Otawara-Shi, Tochigi-Ken (JP)

(72) Inventors: Kazuya Tanoue, Tochigi (JP); Takao Kasugai, Tochigi (JP); Shinya Ozawa, Tochigi (JP)

(73) Assignee: TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 18 days.

(21) Appl. No.: 16/379,123

(22) Filed: Apr. 9, 2019

(65) Prior Publication Data
US 2019/0231276 A1    Aug. 1, 2019

Related U.S. Application Data

(63) Continuation of application No. 14/868,571, filed on Sep. 29, 2015, now Pat. No. 10,285,653, which is a
(Continued)

(30) Foreign Application Priority Data

Mar. 29, 2013    (JP) .................................. 2013-073787

(51) Int. Cl.
*A61B 5/00*    (2006.01)
*G01R 33/54*    (2006.01)
(Continued)

(52) U.S. Cl.
CPC ............ *A61B 5/7275* (2013.01); *A61B 5/055* (2013.01); *A61B 5/742* (2013.01); *A61B 5/7445* (2013.01);
(Continued)

(58) Field of Classification Search
CPC ....... A61B 5/7275; A61B 5/742; A61B 5/055; A61B 5/7445; G01R 33/543; G01R 33/288; G01R 33/546
See application file for complete search history.

(56) References Cited

U.S. PATENT DOCUMENTS 5,349,296 A * 9/1994 Cikotte .................. G01R 33/54
324/309
5,861,865 A * 1/1999 Anand .................... A61B 5/055
174/350
(Continued)

FOREIGN PATENT DOCUMENTS

CN       101840464 A    9/2010
JP       5-317287       12/1993
(Continued)

OTHER PUBLICATIONS

International Search Report for PCT/JP2014/058976 dated Apr. 28, 2014, two pages.
(Continued)

*Primary Examiner* — Daniel R Miller
(74) *Attorney, Agent, or Firm* — Nixon & Vanderhye P.C.

(57) ABSTRACT

In one embodiment, a magnetic resonance imaging apparatus configured to sequentially execute plural imaging sequences includes: processing circuitry configured to calculate a predicted value of Long MR Examination specific absorbed energy which is an accumulated SAR (Specific Absorption Ratio) value over the plural imaging sequences; and a display configured to display information on the predicted value with respect to a predetermined safety reference value of the Long MR Examination specific absorbed energy.

9 Claims, 13 Drawing Sheets

Related U.S. Application Data continuation of application No. PCT/JP2014/058976, filed on Mar. 27, 2014.

(51) Int. Cl.
*A61B 5/055* (2006.01)
*G01R 33/28* (2006.01)

(52) U.S. Cl.
CPC ......... *G01R 33/288* (2013.01); *G01R 33/543* (2013.01); *G01R 33/546* (2013.01)

(56) References Cited

U.S. PATENT DOCUMENTS

| | | | |
|---|---|---|---|
| 6,687,527 | B1 | 2/2004 | Wu |
| 7,355,404 | B1* | 4/2008 | Hariharan ............ G01R 33/543 |
| | | | 324/307 |
| 7,741,624 | B1* | 6/2010 | Sahadevan ........... A61N 5/1081 |
| | | | 250/341.7 |
| 2009/0234218 | A1* | 9/2009 | Washburn .............. A61B 5/055 |
| | | | 600/410 |
| 2009/0274353 | A1* | 11/2009 | Martin .................. G01R 33/54 |
| | | | 382/131 |
| 2010/0152817 | A1* | 6/2010 | Gillbe .................. A61N 1/0551 |
| | | | 607/72 |
| 2010/0239069 | A1 | 9/2010 | Bourdeaux et al. |
| 2011/0148412 | A1 | 6/2011 | Kanazawa |
| 2012/0238861 | A1 | 9/2012 | Gebhardt |
| 2013/0023753 | A1 | 1/2013 | Kawamura et al. |
| 2013/0053678 | A1* | 2/2013 | Vitek ....................... A61N 7/02 |
| | | | 600/411 |
| 2013/0243165 | A1 | 9/2013 | Bourdeaux et al. |
| 2016/0015326 | A1 | 1/2016 | Tanoue |

FOREIGN PATENT DOCUMENTS

| | | |
|---|---|---|
| JP | 2001-190516 | 7/2001 |
| JP | 2011-143235 | 7/2011 |
| JP | 2012/187406 A | 10/2012 |
| JP | 2013/031633 A | 2/2013 |
| JP | 2014-14391 | 1/2014 |
| WO | WO 2011/122430 | 10/2011 |

OTHER PUBLICATIONS

Chinese office action dated Jun. 2, 2017, in Patent Application No. CN 201480019127.6.
JP Office Action dated Sep. 26, 2017 in JP 2016-238026.
IEC 60601-2-33, Medical electrical equipment—Part 2-33: Particular requirements for the basic safety and essential performance of magnetic resonance equipment for medical diagnosis, 2010.
Radio Frequency Field, William Faulkner and Associates, 2009, p. 13, available at www.t2star.com/faulkner/MRSO_Gourse/files_files/6_rf_v9_3-1.pdf.
Gorny et al., Calorimetric calibration of head coil SAR estimates displayed on a clinical MR scanner, Phys. Med. Biol. 53 (2008) 2565-2576.

* cited by examiner

EXAMPLE OF SETTING SCREEN OF EXAMINATION CONTENTS
(IMAGING CONDITIONS ETC.)

SC1

PATIENT A    EXAMINATION (1)

Plan  Start  DISPLAY SAE  DISPLAY SAE GRAPH

W1

| IMAGING SEQUENCE NUMBER | IMAGING SEQUENCE ID | Time | Plan |
|---|---|---|---|
| 1 | Locator 3 Axis | 2:00 | |
| 2 | Shimming | 4:00 | |
| 3 | MAP | 3:00 | |
| 4 | 3D TOF | 5:00 | ✓ |
| 5 | T2W AX | 3:00 | |
| 6 | Flair AX | 5:00 | |
| 7 | T1 IR AX | 5:00 | |
| 8 | T2*W AX | 3:00 | |
| 9 | T1W AX SE | 5:00 | |

SETTING OF PARAMETER VALUES FOR IMAGING SEQUENCE NUMBER "4"

W2

Basic | Advance

| SLICE NUMBER | 20 | SLICE GAP | 1.2 |
| SLICE THICKNESS | 6.00 | PHASE ENCODE DIRECTION | Y |
| SLICE CENTER OFFSET | 200.0 | PE FOV | 22.0 |
| SLICE DIRECTION | AXIAL | RO FOV | 22.0 |

FIG. 4

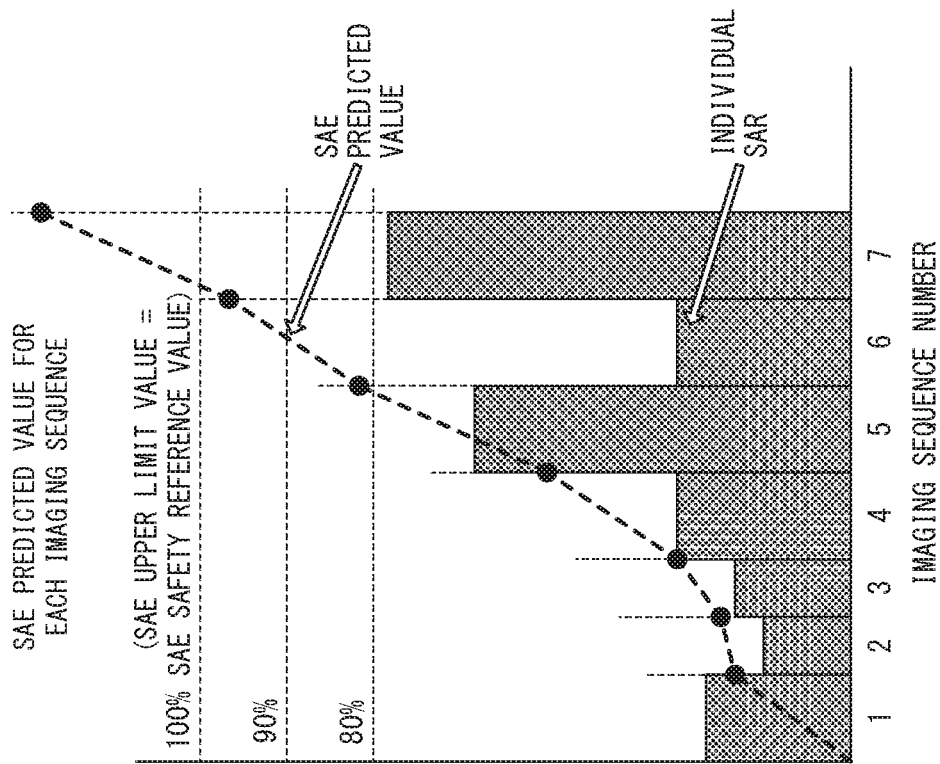
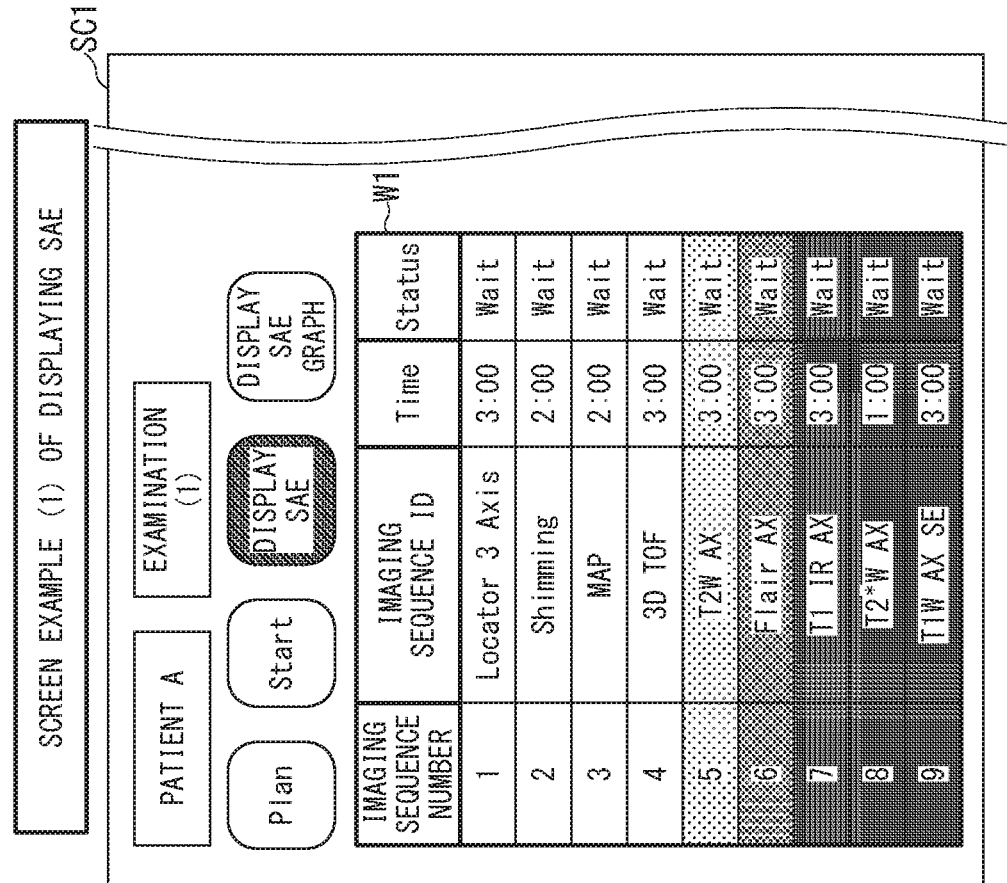
FIG. 5B
FIG. 5A

MAGNETIC RESONANCE IMAGING APPARATUS

CROSS-REFERENCE TO RELATED APPLICATIONS

This application is a Continuation Application of No. PCT/JP2014/58976 filed on Mar. 27, 2014, and the PCT application is based upon and claims the benefit of priority from Japanese Patent Application No. 2013-73787, filed on Mar. 29, 2013, the entire contents of which are incorporated herein by reference.

FIELD

Embodiments described herein relate generally to a magnetic resonance imaging apparatus.

BACKGROUND

A magnetic resonance imaging apparatus is an imaging apparatus which excites nuclear spin of an object placed in a static magnetic field with an RF (Radio Frequency) signal having the Larmor frequency and reconstructs an image based on magnetic resonance signals emitted from the object due to the excitation.

In imaging with the use of a magnetic resonance imaging apparatus, radio frequency (RF) signals are applied to an object in order to obtain magnetic resonance signals. Application of radio frequency signals heats up an object and increases body temperature of the object. For the above reason, SAR (Specific Absorption Ratio) is defined as energy absorbed per unit mass of an object from the perspective of safety. In addition, upper limit values of SAR, i.e. safety reference values of SAR are defined in IEC (International Electrotechnical Commission) standards (IEC60601-2-33).

More specifically, SAR (its unit is W/kg) is defined as energy of RF signal(s) absorbed by one kilogram of biological tissue. An upper limit value of time average SAR in arbitrary ten seconds and an upper limit value of time average SAR in the last six minutes are also defined for each imaging part such as the whole body, the head part, etc. Hereinafter, the above-described time average SAR in arbitrary ten seconds is simply referred to as 10-second average SAR, and the above-described time average SAR in the last six minutes is simply referred to as 6-minute average SAR.

Meanwhile, in magnetic resonance imaging of an object, combining plural imaging sequences and consecutively executing the respective imaging sequences in the combined order is generally performed. In general, the above-described SAR is different depending on each imaging sequence. In addition, an imaging time of an individual imaging sequence may be shorter than six minutes in many cases. Therefore, the 6-minute average SAR is different depending on the execution order of imaging sequences. Japanese Patent Application Laid-open Publication No. 2011-143235 discloses technology of automatically determining execution order of imaging sequences so that the 6-minute average SAR does not exceed its upper limit value when plural imaging sequences are performed.

Recently, upper limit values of "long MR examination specific absorbed energy" are newly defined in the third edition of IEC60601-2-33 of IEC standards, in addition to the above-described 10-second average SAR and 6-minute average SAR. This is a rule that continuation of an examination is prohibited when the total amount (i.e. an accumulated value or an integrated value) of SAR of this examination exceeds the upper limit value of the total amount of SAR for one examination. Hereinafter, long MR examination specific absorbed energy is simply referred to as SAE (Specific Absorbed Energy).

When SAE of a certain examination exceeds its upper limit value, this examination cannot be continued under the above-described rule even if this examination is in progress. The possibility that SAE reaches its upper limit value is high, especially (a) when an examination requiring a long imaging time such as whole body imaging is performed and (b) when imaging is interrupted on the way and then imaging is resumed.

For the above reasons, a magnetic resonance imaging apparatus, whereby a user such as an inspection engineer or a doctor can easily recognize relationship between an SAR value and its upper limit value not only in a planning stage of an examination but also in the middle of an examination, has been desired.

BRIEF DESCRIPTION OF THE DRAWINGS

FIG. 4 is a chart showing an example of display for setting examination contents;

FIG. 5A is a chart showing the first example of display of SAE predicted values;

FIG. 5B is a chart showing an example of concept of calculating SAE predicted values in FIG. 5A;

DETAILED DESCRIPTION

According to one embodiment, a magnetic resonance imaging apparatus configured to sequentially execute plural imaging sequences includes: processing circuitry configured to calculate a predicted value of Long MR Examination specific absorbed energy which is an accumulated SAR value over the plural imaging sequences; and a display configured to display information on the predicted value with respect to a predetermined safety reference value of the Long MR Examination specific absorbed energy.

Hereinafter, embodiments of the present disclosure will be explained with reference to the accompanying drawings.

(1) Configuration and General Operation

Figure 1:
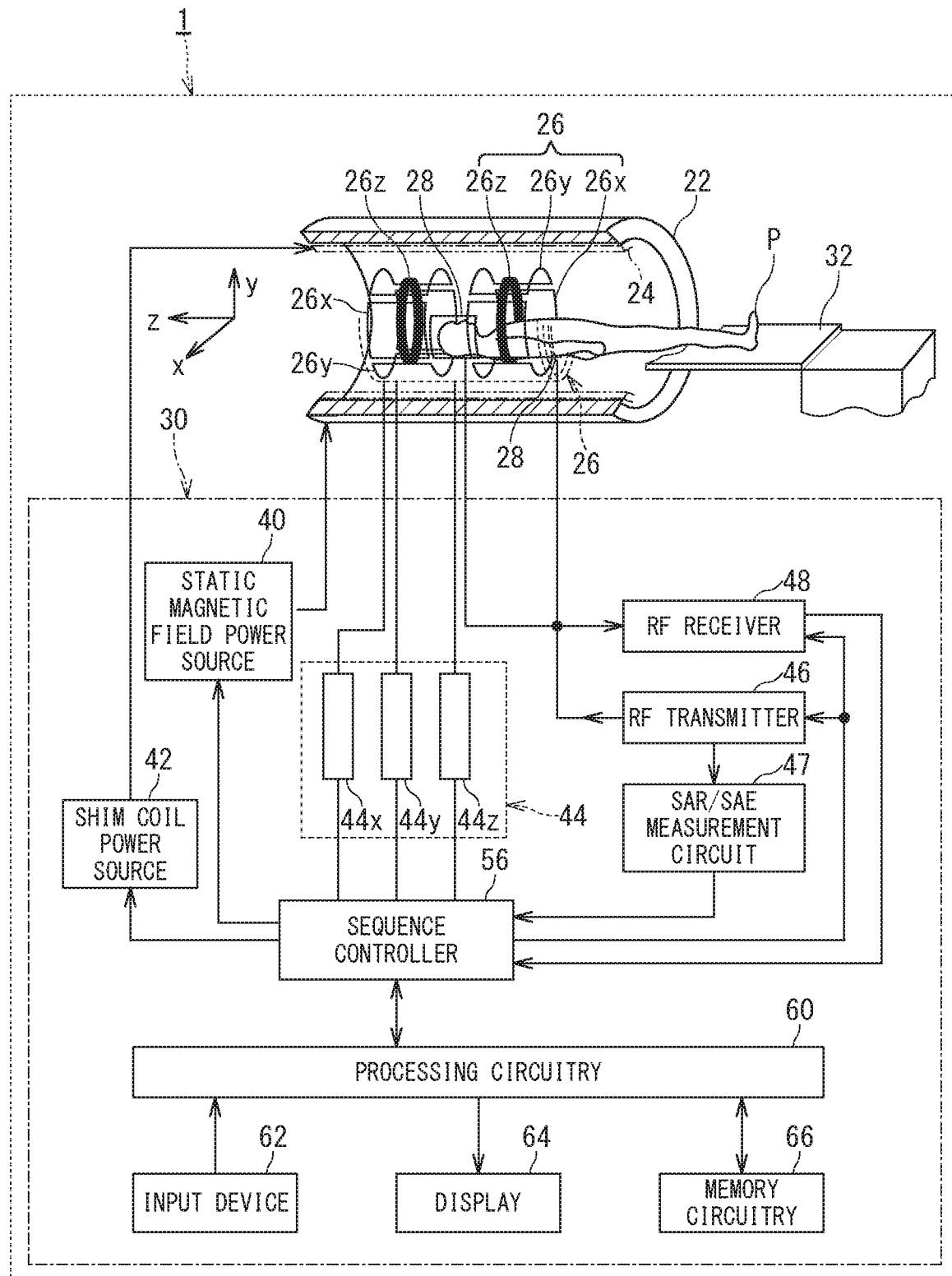
FIG. 1 is a block diagram showing an example of overall configuration of a magnetic resonance imaging apparatus of one embodiment.

FIG. 1 is a block diagram showing an example of overall configuration of a magnetic resonance imaging apparatus 1 of the present embodiment. As shown in FIG. 1, the magnetic resonance imaging apparatus 1 includes a cylindrical static magnetic field magnet 22 forming a static magnetic field, a cylindrical shim coil 24 coaxially arranged inside the static magnetic field magnet 22, a gradient coil 26, an RF coil 28 in addition to a control system 30 and a bed 32 on which an object (e.g., a patient) P is loaded etc. Furthermore, the control system 30 includes a static magnetic field power source 40, a shim coil power source 42, a gradient coil power source 44, an RF transmitter 46, an SAR/SAE measurement circuit 47, an RF receiver 48, a sequence controller 56, processing circuitry 60, an input device 62, a display 64, memory circuitry 66, etc.

The static magnetic field magnet 22 is connected to the static magnetic field power source 40, and forms a static magnetic field in an imaging space by consuming an electric current supplied from the static magnetic field power source 40. The shim coil 24 is connected to the shim coil power source 42, and uniforms the static magnetic field by consuming electric currents supplied from the shim coil power source 42. The static magnetic field magnet 22 is configured as a superconductive coil in many cases, and is supplied with an electric current by being connected to the static magnetic field power source 40 at the time of excitation. However, once it is excited, the static magnetic field magnet 22 is generally brought into a non-connected state. In addition, the static magnetic field magnet may be configured as a permanent magnet, instead of providing the static magnetic field power source 40.

The gradient coil power source 44 includes an X axis gradient coil power source 44x, a Y axis gradient coil power source 44y, and a Z axis gradient coil power source 44z. In FIG. 1, the direction of the common axis of the static magnetic field magnet 22 and the shim coil 24 is assumed to be the Z axis direction, the vertical axis is assumed to be the Y axis direction, and the direction orthogonal to each of those Z axis direction and the Y axis direction is assumed to be the X axis direction.

The gradient coil 26 includes an X axis gradient coil 26x, a Y axis gradient coil 26y, and a Z axis gradient coil 26z. The gradient coil 26 is shaped in the form of a cylinder inside the static magnetic field magnet 22. The X axis gradient coil 26x, the Y axis gradient coil 26y, and the Z axis gradient coil 26z are connected to the X axis coil power source 44x, the Y axis gradient coil power source 44y, and the Z axis gradient coil power source 44z, respectively.

The X axis gradient coil 26x forms a gradient magnetic field Gx in the X axis direction in the imaging space by consuming an electric current supplied from the X axis gradient coil power source 44x. Similarly, the Y axis gradient coil 26y forms a gradient magnetic field Gy in the Y axis direction in the imaging space by consuming an electric current supplied from the Y axis gradient coil power source 44y. Further similarly, the Z axis gradient coil 26z forms a gradient magnetic field Gz in the Z axis direction in the imaging space by consuming an electric current supplied from the Z axis gradient coil power source 44z.

Thereby, a gradient magnetic field Gss in a slice selection direction, a gradient magnetic field Gpe in a phase encode direction, and a gradient magnetic field Gro in a readout (frequency encode) direction can be arbitrarily set as logical axes, by combining the gradient magnetic fields Gx, Gy, and Gz in the three axial directions of the apparatus coordinate system. Each gradient magnetic field is superimposed on the static magnetic field. Hereinafter, the coordinate system configured of the slice selection direction, the phase encode direction, and the readout direction is referred to as an image coordinate system.

The RF transmitter 46 generates RF pulses of the Larmor frequency for causing nuclear magnetic resonance based on control information inputted from the sequence controller 56, and transmits the generated RF pulses to the RF coil 28. The RF coil 28 includes a WBC (Whole body coil) which applies RF pulses to the object P and receives MR signals from the object P, a receive-only coil (so-called local coil) disposed in the bed 32 or adjacent to an object P, etc.

The MR signals received by the RF coil 28 are transmitted to the RF receiver 48 via a signal cable.

The RF receiver 48 generates k-space data which are digitized complex data of the MR signals, by performing various types of signal processing on the received MR signals and then performing A/D (analogue to digital) conversion on the MR signals subjected to the various types of signal processing. The above various types of signal processing include pre-amplification, intermediate frequency conversion, phase detection, low frequency amplification, filtering, etc. The RF receiver 48 outputs the generated k-space data of the MR signals to the sequence controller 56.

The SAR/SAE measurement circuit 47 measures RF power applied to a patient by detecting output of the RF transmitter 46 as an example, and acquires actual measured values of SAR and SAE based on the measured RF power. The SAR/SAE measurement circuit 47 transmits the measured values of SAR and SAE to the processing circuitry 60 via the sequence controller 56.

The sequence controller 56 generates data rows and control information for generating the gradient magnetic fields Gx, Gy, and Gz and RF pulses corresponding to imaging conditions including a determined pulse sequence, under the control of the processing circuitry 60. The sequence controller 56 outputs those data rows and control information to each of the X axis gradient coil power source 44x, the Y axis gradient coil power source 44y, the Z axis gradient coil power source 44z, and the RF transmitter 46.

In addition, the sequence controller 56 acquires the MR signals received in response to the above gradient magnetic fields Gx, Gy, and Gz and RF pulses from the RF receiver 48 as the k-space data, and outputs the k-space data to the processing circuitry 60.

The processing circuitry 60 controls the entirety of the magnetic resonance imaging apparatus 1. In addition, the processing circuitry 60 performs setting and change of examination contents based on various setting information items entered into the input device 62 by a user's manipulation, and controls the sequence controller 56 based on the selected or changed examination contents.

Further, the processing circuitry 60 generates image data by performing reconstruction processing including inverse Fourier conversion etc. on the k-space data inputted from the sequence controller 56. In other words, the processing circuitry 60 functions as a reconstruction unit. The generated image data are displayed on the display 64.

Moreover, the processing circuitry 60 of the present embodiment calculates a predicted value of long MR examination specific absorbed energy (hereinafter, referred to as an SAE predicted value), based on the determined examination contents. In addition, the processing circuitry 60 updates an SAE predicted value based on an actual measured value of long MR examination specific absorbed energy (hereinafter, referred to as an SAE measured value) determined by the SAR/SAE measurement circuit 47. More detailed methods of calculating an SAE predicted value and updating an SAE predicted value will be described below.

Figure 2:
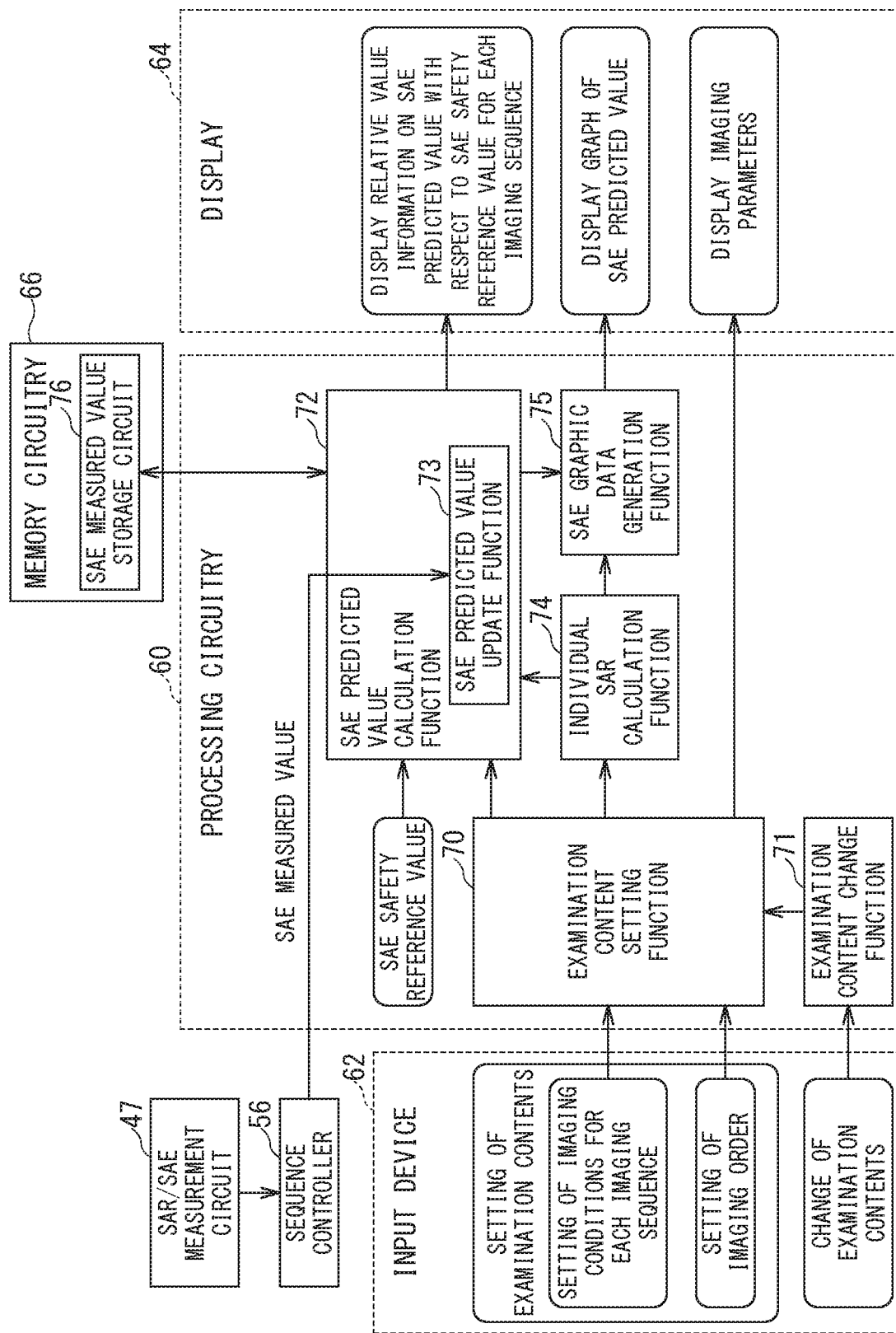
FIG. 2 is a functional block diagram showing an example of configuration of main components relevant to calculation of SAE and display of SAE.

FIG. 2 is a functional block diagram showing an example of configuration of components relevant to calculation and display of SAE predicted values, out of various types of processing executed by the processing circuitry 60 of the magnetic resonance imaging apparatus 1 of the present embodiment.

The processing circuitry 60 includes structure for computational processing such as a processor etc., for example. The processing circuitry 60 has various functions such as an examination content setting function 70, an examination content change function 71, an SAE predicted value calculation function 72, an SAE predicted value update function 73, an individual SAR calculation function 74, and an SAE graphic data generation function 75. The processing circuitry 60 achieves or implements each of the above-described functions by executing one or more programs stored in the memory circuitry 66 or one or more programs directly stored in a circuit of the processor in the processing circuitry 60.

Figure 3:
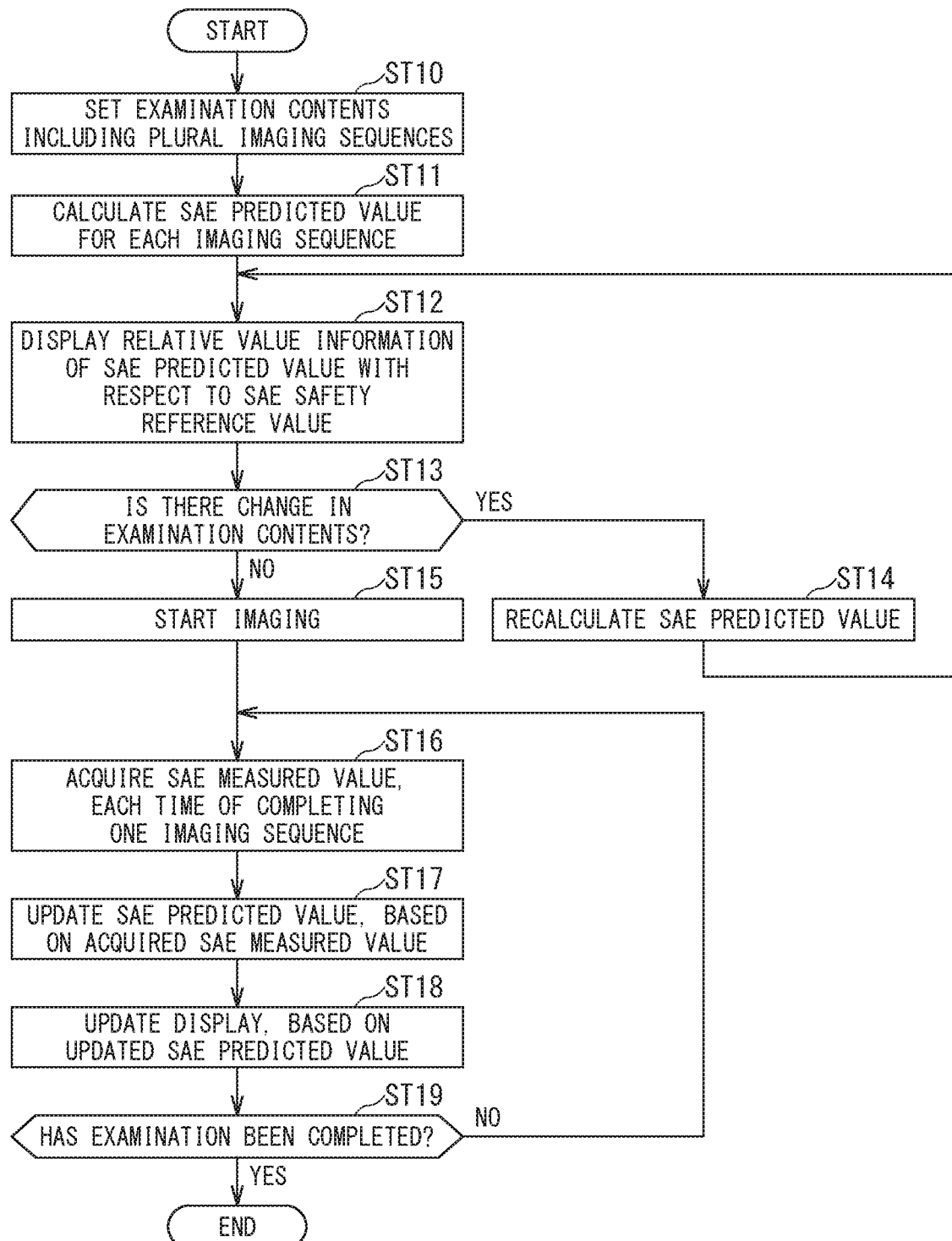
FIG. 3 is a flowchart showing an example of processing relevant to calculation of SAE and display of SAE.

FIG. 3 is a flowchart showing an example of processing relevant to calculation of SAE predicted values and display of SAE predicted values, out of various types of processing performed by the magnetic resonance imaging apparatus 1 of the present embodiment.

Hereinafter, the operation of the magnetic resonance imaging apparatus 1 of the present embodiment will be explained in the order of the flow in FIG. 3 with reference to FIG. 2 as a functional block diagram.

(2) Setting of Examination Contents

First, in the step ST10 of FIG. 3, examination contents including plural imaging sequences are set. The examination content setting function 70 of the processing circuitry 60 acquires various types of setting information items inputted via input tools such as a keyboard, a mouse, etc. of the input device 62. The setting information items inputted from the input device 62 include identification information of a certain patient, identification information of an examination performed on this patient, identification information of plural imaging sequences included in this examination, information on an imaging time of each imaging sequence, and information on execution temporal order of the respective imaging sequences.

Here, "an imaging sequence" means an individual sequence of imaging such as T1 weighted imaging, T2 weighted imaging, and so forth. In addition, each of an imaging for obtaining locators, an imaging for shimming, an imaging for generating a map, etc. is treated as one imaging sequence. An imaging sequence is also called "a series" under hierarchy management of DICOM (Digital Imaging and Communication in Medicine) standards.

The examination content setting function 70 of the processing circuitry 60 determines various pulse sequences based on information inputted from the input device 62 such as an identification of each imaging sequence, an imaging time of each imaging sequence, execution temporal order of the respective imaging sequences, etc. The examination content setting function 70 outputs the determined pulse sequences to the sequence controller 56.

In addition, the examination content setting function 70 outputs the information on imaging conditions such as the identification of each imaging sequence, the imaging time of each imaging sequence, the execution order of the respective imaging sequences, a pulse sequence of each imaging sequence, etc. to the display 64. Thereby, the examination content setting function 70 makes the display 64 display the above information on imaging condition.

FIG. 4 is a chart showing an example of display on the screen SC1 of the display 64 in the stage of setting examination contents.

An examination content window W1 is displayed on the left side of the screen SC1 and a parameter setting window W2 is displayed on the right side of the screen SC1. The example of FIG. 4 shows that an examination (1) is performed on a patient A and imaging of nine imaging sequences from the imaging sequence number 1 to 9 is executed in the order arranged in the examination content window W1 as the contents of the examination (1).

The imaging sequence 1 (imaging sequence ID: Locator 3 Axis) in the first line of the examination content window W1 shows that one locator is imaged in each of the X axis direction, the Y axis direction, and the Z axis direction and its total imaging time is two minutes as indicated by 2:00 in the Time column, for example.

The imaging sequence 2 (imaging sequence ID: Shimming) in the second line of the examination content window W1 shows that imaging for adjusting uniformity of the static magnetic field is performed for four minutes as indicated by 4:00 in the Time column.

The imaging sequence 3 (imaging sequence ID:MAP) in the third line of the examination content window W1 shows that imaging for acquiring sensitivity distribution maps of surface coils is performed for three minutes as indicated by 3:00 in the Time column.

The imaging sequence 4 (imaging sequence ID:3D TOF) in the fourth line of the examination content window W1 shows that imaging under a TOF (Time of Flight) technique for obtaining a three-dimensional image is performed for five minutes as indicated by 5:00 in the Time column.

Likewise, the imaging sequence 5 (imaging sequence ID: T2W AX) in the fifth line shows that T2 weighted imaging of axial planes is performed for three minutes as an example, and the rest of the examination content window W1 can be interpreted in the similar manner.

On the right side of the screen SC1, the parameter setting window W2 that indicates concrete parameters of the imaging sequence selected in the examination content window W1 is displayed. Selection of an imaging sequence is performed by clicking a corresponding part in the Plan column of the examination content window W1. In the box of the selected imaging sequence in the Plan column, a check mark is added. In the example of FIG. 4, the imaging sequence 4 is selected and parameters (slice number, slice thickness, etc.) preliminarily set for the pulse sequence of the imaging sequence 4 (imaging sequence ID: 3D TOF) are displayed in the parameter setting window W2. Values of the displayed parameters can be individually changed.

(3) Calculation and Display of SAE Predicted Value (First Embodiment)

When setting of the examination contents are completed, an SAE predicted value is calculated in the next step ST11 (see FIG. 3). Calculation of an SAE predicted value is executed by the SAE predicted value calculation function 72 of the processing circuitry 60 shown in FIG. 2. Moreover, the SAE predicted value calculation function 72 calculates information on the calculated SAE predicted value with respect to the SAE safety reference value defined as an upper limit value, based on this SAE safety reference value and the calculated SAE predicted value.

The SAE predicted value calculation function 72 calculates relative value information of the calculated SAE predicted value with respect to the SAE safety reference value, for example. The relative value information of the calculated SAE predicted value with respect to the SAE safety reference value means the ratio of the calculated SAE predicted value to the SAE safety reference value and is a value obtained by dividing the calculated SAE predicted value by the SAE safety reference value shown by percentage, for example.

In the step ST12, the information on the calculated SAE predicted value with respect to the SAE safety reference value determined in the step ST11 is displayed on the display 64.

FIG. 5B is a chart showing concept of calculating an SAE predicted value and a relative value of an SAE predicted value with respect to the SAE safety reference value. In addition, FIG. 5A is a chart showing the first example of display of relative value information of an SAE predicted value with respect to the SAE safety reference value.

In FIG. 5B, individual SAR for each imaging sequence is indicated by a bar graph, and SAE predicted values are indicated by a polygonal line graph of a bold broken line. SAE predicted values are calculated from individual SAR.

As mentioned above, SAR (its unit is W/kg) is defined as energy of RF signal(s) absorbed in one kilogram of biological tissue. A value obtained by dividing an energy value of RF signal(s) absorbed in one kilogram of biological tissue during arbitrary ten seconds by ten seconds is the 10-second average SAR (W/kg) defined by IEC. A value obtained by dividing an energy value of RF signal(s) absorbed in one kilogram of biological tissue during the last six minutes by six minutes is the 6-minute average SAR (W/kg).

By contrast, the above-described "individual SAR" is a value obtained by dividing an energy value of RF signal(s) absorbed in one kilogram of biological tissue by the imaging time T when an individual imaging sequence is consecutively performed for the imaging time T. When an imaging sequence including a predetermined pulse sequence is performed for the imaging time T, the energy of RF signals absorbed in one kilogram of biological tissue becomes larger as the imaging time T becomes larger. In this case, the value obtained by dividing this energy value by the imaging time T becomes a value independent of the imaging time T and indicates an individual average SAR value for each imaging sequence. This value is defined as the individual SAR.

If the pulse sequence for each imaging sequence is determined, the individual SAR can be calculated for each imaging sequence based on specifications of RF pulse trains (power, pulse width, and pulse cycle etc. of each RF pulse) included in the pulse sequence. In addition, when specifications of RF pulse trains for each imaging sequence are preliminarily fixedly determined, the individual SAR may be calculated with reference to a table in which type of imaging sequence and individual SAR values are associated with each other. As to power of each RF pulse, a preliminarily measured value may be used and a value determined in a calibration scan executed before start of an examination may be used. Calculation of individual SAR values is performed by the individual SAR calculation function 74 of the processing circuitry 60 (see FIG. 2).

The SAE predicted value is a value obtained by accumulating individual SAR values, in other words, a value obtained by time-integrating the individual SAR. Thus, if the individual SAR value for each imaging sequence, an imaging time of each imaging sequence, and the execution order of the respective imaging sequences are determined, the SAE predicted values can be calculated. Here, the SAE predicted value for each imaging sequence is defined as an SAE predicted value at the time when each imaging sequence is completed. In FIG. 5B, the SAE predicted value for each imaging sequence is indicated by a filled black circle.

Meanwhile, the SAE safety reference value (the upper limit value of SAE) is defined as total quantity of SAR for the whole body in the case of consecutively imaging 4 W/kg ((Whole body SAR 4 W/kg), (the upper limit value of the 6-minute SAR 1st Operation Mode)) of biological tissue for one hour.

The SAE predicted value calculation function 72 of the processing circuitry 60 calculates information on an SAE predicted value with respect to the SAE safety reference value. For example, the SAE predicted value calculation function 72 calculates a relative value of an SAE predicted value with respect to the SAE safety reference value as a ratio shown by percentage, by dividing the absolute value of the calculated SAE predicted value by the SAE safety reference value. The relative value of an SAE predicted value with respect to the SAE safety reference value is preferably calculated for each imaging sequence.

Moreover, the SAE predicted value calculation function 72 sorts ratios of respective SAE predicted values with respect to the SAE safety reference value (hereinafter, referred to as an SAE predicted value ratio) into appropriately separated segments. For example, the calculated ratios are sorted under the assumption that the first segment is 0% or more but less than 80%, the second segment is 80% or more but less than 90%, the third segment is 90% or more but less than 100%, and the fourth segment is 100% or more. Afterward, the SAE predicted value calculation function 72 outputs the relative value information of the SAE predicted value of each imaging sequence with respect to the safety reference value (for example, information on which of the first to fourth segments each imaging sequence belongs to) to the display 64.

The display 64 displays the above-described relative value information of each SAE predicted value with respect to the safety reference value, in addition to display of an identification of each imaging sequence. Detailed meaning of this operation is as follows.

Firstly, an identification of each imaging sequence means the display row of each imaging sequence in the examination content window W1 and a character string belonging to each imaging sequence.

Secondly, to display the relative value information of each SAE predicted value with respect to the safety reference value in addition to an identification of each imaging sequence means, for example, to display the display row and the character string of each imaging sequence in different aspects depending on which of the first to fourth segments each imaging sequence belongs to. As examples of the above-described (mutually) different aspects of display, display in different chromatic colors, display in different shading, etc. are included.

In the example of FIG. 5B, the SAE predicted value ratios of the four imaging sequences of imaging sequence number 1 to 4 are less than 80%, and thus they belong to the first segment. The SAE predicted value ratio of the imaging sequence of imaging sequence number 5 is over 80% but less than 90%, and thus it belongs to the second segment. The SAE predicted value ratio of the imaging sequence of imaging sequence number 6 is over 90% but less than 100%, and thus it belongs to the third segment. The SAE predicted value ratio of the imaging sequence of imaging sequence number 7 is over 100%, and thus it belongs to the fourth segment. The SAE predicted value ratios of the imaging sequences of imaging sequence number 8 and 9 are obviously over 100%, and thus they belong to the fourth segment.

For the above reasons, in the first display example shown in FIG. 5A, the display 64 displays the three imaging sequences of imaging sequence number 7 to 9 sorted into the fourth segment by red or the darkest gray-scale. In addition, the display 64 displays the imaging sequence of imaging sequence number 6 sorted into the third segment by yellow or gray-scale brighter than the imaging sequence number 7 to 9. Moreover, the display 64 displays the imaging sequence of imaging sequence number 5 sorted into the second segment by green or further brighter gray-scale. Furthermore, the display 64 displays the imaging sequences of imaging sequence number 1 to 4 sorted into the first segment by background color without adding shading or changing color.

As explained above, the processing circuitry 60 and the display 64 changes a display aspect of each imaging sequence depending on its SAE predicted value ratio. Thereby, a user can easily recognize an SAE predicted value of which imaging sequence is most likely to exceed the SAE safety reference value. In addition, even if an SAE predicted value of any one of the imaging sequences does not exceed the SAE safety reference value, a user can easily recognize to what extent each SAE predicted value is close to the SAE safety reference value. As a result, a user can appropriately change examination contents as needed basis before start of imaging.

Figure 6B:
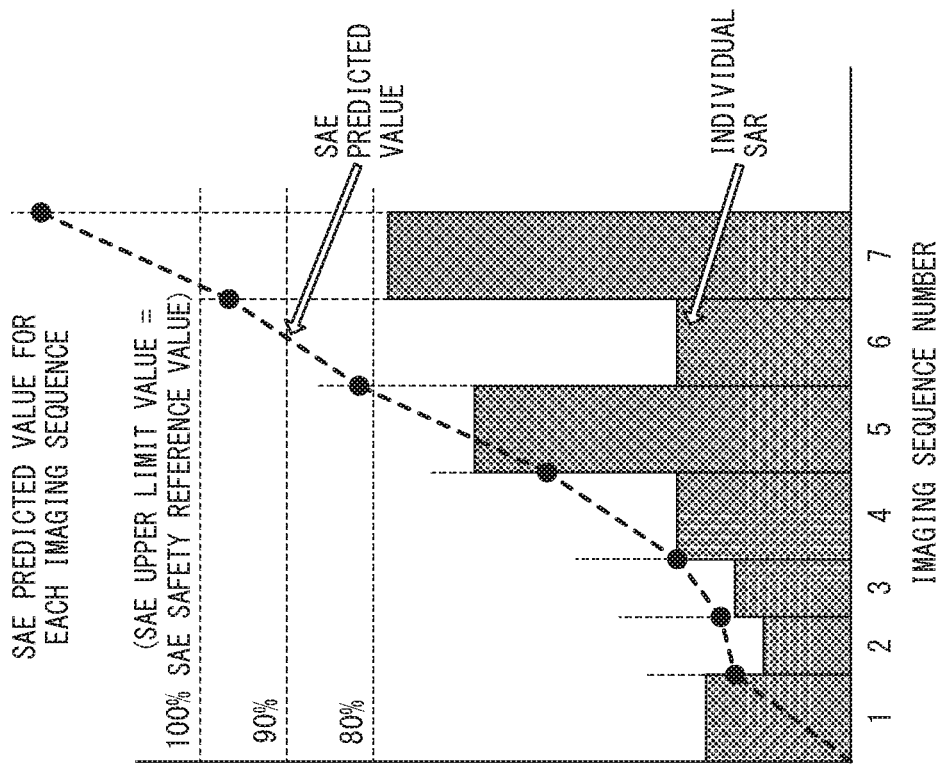
FIG. 6B is a chart showing an example of concept of calculating SAE predicted values in FIG. 6A.
Figure 6A:
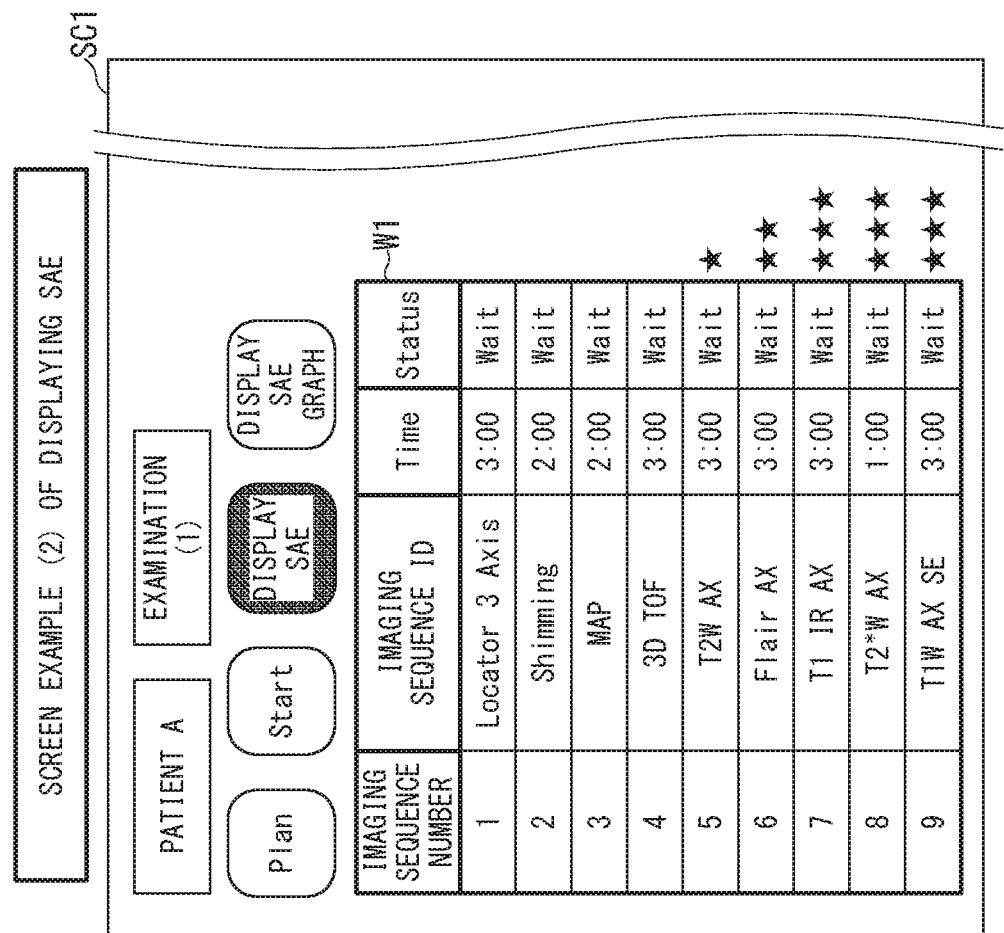
FIG. 6A is a chart showing the second example of display of SAE predicted values.

FIG. 6A is a chart showing the second display example of SAE predicted value ratios. FIG. 6B is the same as FIG. 5B. In the second display example, an icon, whose aspect is different depending on the SAE predicted value ratio, is displayed adjacent to the display region of an identification of each imaging sequence. Each imaging sequence (number 1 to 4) of the first segment is distinguished from other segments by omitting the icon, and one star icon is displayed for each imaging sequence (number 5) of the second segment. In addition, two star icons are displayed for each imaging sequence (number 6) of the third segment, and three star icons are displayed for each imaging sequence (number 7 to 9) of the fourth segment.

The variable factor of display aspect for each imaging sequence in accordance with its SAE predicted value is not limited to gray-scale, chromatic color, and number of icons as mentioned above, but various display aspects to be supposed by a person having ordinary skill in the art can be used.

Figure 7:
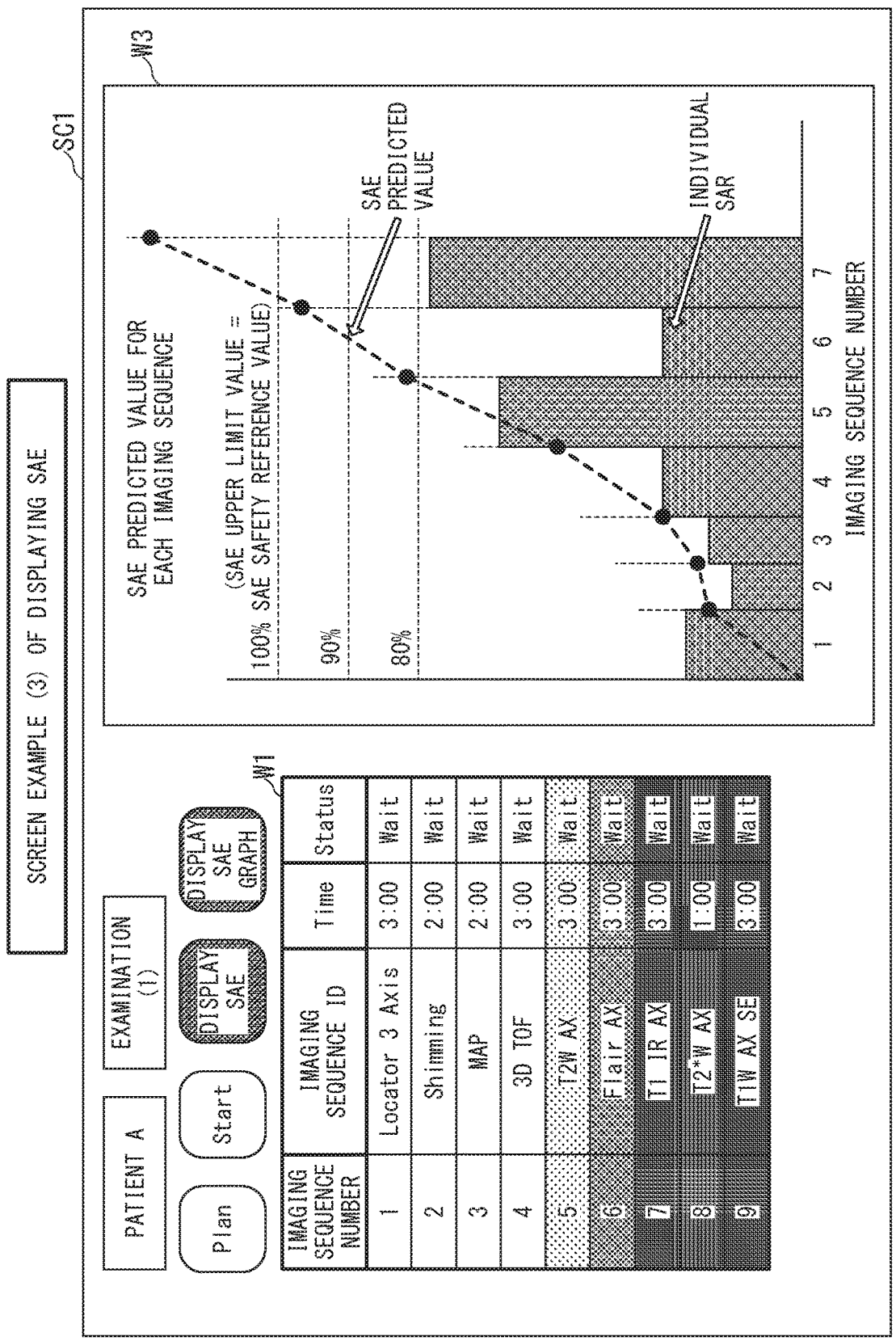
FIG. 7 is a chart showing the third example of display of SAE predicted values.

FIG. 7 is the third display example of SAE predicted value ratios. In the third display example, a graph display window W3 is separately provided in addition to display of SAE predicted value ratios in the examination content window W1. In this graph display window W3, a graph indicating SAE predicted values (or SAE predicted value ratios) is displayed in association with the SAE safety reference value. The displayed graph itself is substantially the same as the explanation chart of SAE predicted values (FIG. 5B etc.). Generation of graph data is performed by the SAE graphic data generation function 75 (FIG. 2) of the processing circuitry 60. By displaying this graph, a user can more intuitively understand the correlation between the SAE safety reference value and each SAE predicted value (or each SAE predicted value ratio).

Incidentally, ordinary display like the examination content window W1 in FIG. 4 without adding information on SAE predicted value ratios may be performed in the examination content window W1, so that a graph of SAE predicted values is displayed in parallel with the above-described ordinary display of the examination content window W1.

Returning to FIG. 3, in the step ST13, whether examination contents are changed or not is determined. Determination as to whether examination contents are changed or not and change of examination contents are performed by the examination content change function 71 (FIG. 2) of the processing circuitry 60. When examination contents are changed, the SAE predicted value calculation function 72 recalculates an SAE predicted value depending on the changed contents in the step ST14 and then the processing returns to the step ST12.

Figure 8:
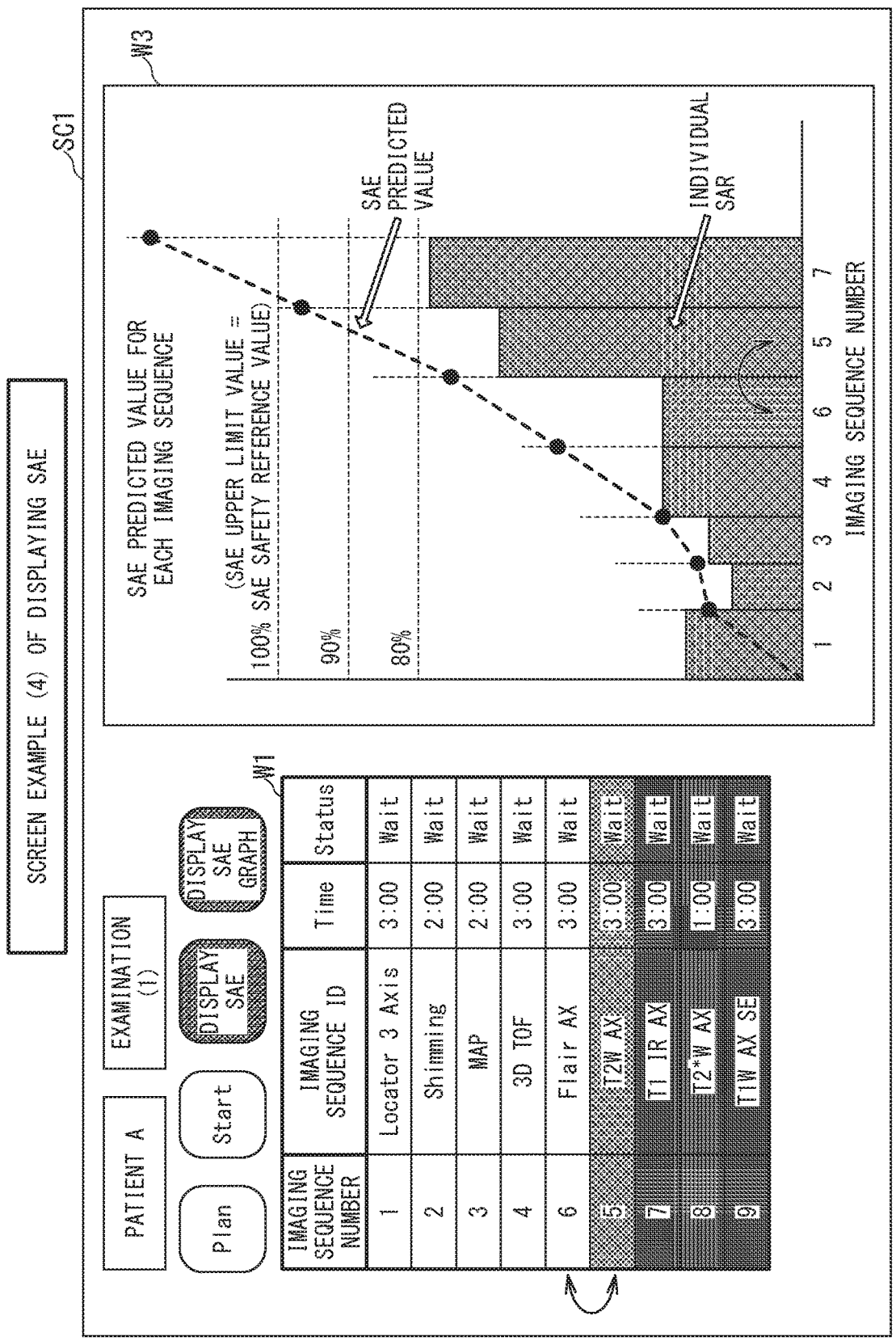
FIG. 8 is a chart showing the fourth example of display of SAE predicted values.

FIG. 8 shows an example in which SAE predicted values are recalculated in association with change of examination contents and display of SAE predicted values are updated based on the recalculated SAE predicted values (or recalculated SAE predicted value ratios). The examination contents shown in FIG. 8 are changed from the examination contents shown in FIG. 7 in that the execution order of the imaging sequence number 5 and the imaging sequence number 6 are replaced each other. As a result, the imaging sequence number 6 is re-sorted into the first segment and thereby the first segment includes the imaging sequence number 6 in addition to imaging sequence number 1 to 4. Moreover, the imaging sequence number 5 is re-sorted from the second segment into the third segment.

Change of examination contents includes change of imaging conditions of each imaging sequence, addition of an imaging sequence, elimination of an imaging sequence, etc. aside from the above-described change of the execution order. When at least one of the examination contents is/are changed, SAE predicted values are recalculated based on the changed content(s) and display is updated based on the recalculated SAE predicted values.

When examination contents are not changed (NO in the step ST13), the processing proceeds to the step ST15 and imaging is started in accordance with the selected or changed examination contents.

Figure 9:
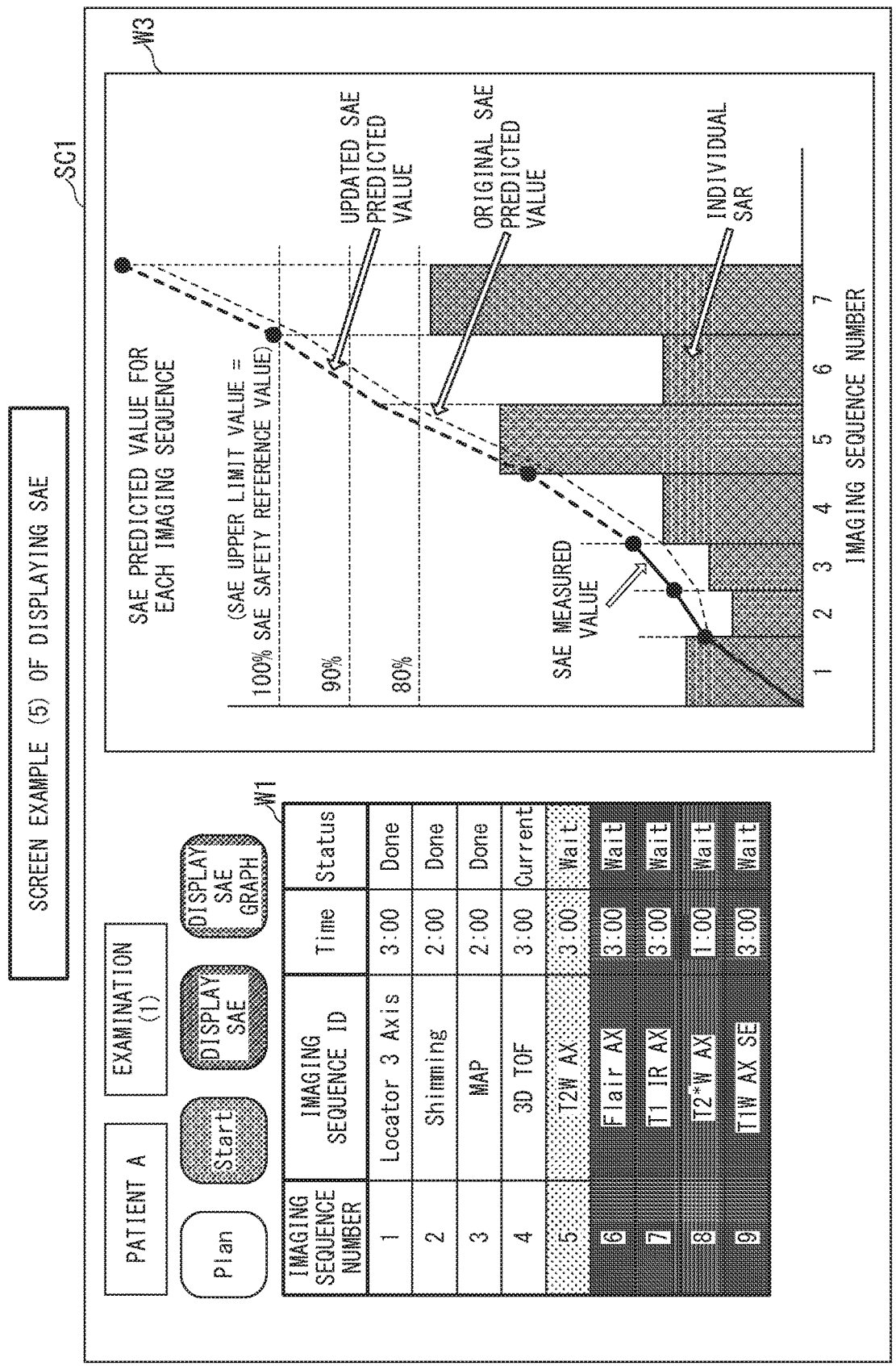
FIG. 9 is a chart showing the fifth example of display of SAE predicted values.

FIG. 9 is a chart showing a display example after start of imaging. "Done" in the status column of the examination content window W1 in FIG. 9 means that imaging of this imaging sequence has been completed. In addition, "Current" in the status column means that imaging of this imaging sequence is currently in progress, and "Wait" in the status column means that this imaging sequence is to be executed from now on.

As soon as imaging is started, the SAR/SAE measurement circuit 47 (FIG. 1 and FIG. 2) measures SAR by measuring RF power and calculates SAE by integrating measured SAR values. The SAR/SAE measurement circuit 47 outputs the calculated SAE as an SAE measured value to the processing circuitry 60 via the sequence controller 56.

The SAE predicted value calculation function 72 of the processing circuitry 60 acquires an SAE measured value at appropriate intervals, for example, each time imaging of one imaging sequence is completed (in the step ST16 in FIG. 3). Then, the SAE predicted value update function 73 of the SAE predicted value calculation function 72 updates the SAE predicted value for each unexecuted imaging sequence based on the acquired SAE measured value, each time of acquiring an SAE measured value (in the step ST17).

Afterward, the SAE graphic data generation function 75 of the processing circuitry 60 and the display 64 update display of the SAE predicted value (i.e. display of relative value information of an SAE predicted value with respect to the SAE safety reference value) for each imaging sequence, based on the updated SAE predicted value (in the step ST18).

Since imaging up to the imaging sequence number 3 is completed in the example of FIG. 9, the polygonal line graph corresponding to the imaging sequence number 1 to 3 in the graph display window W3 indicates SAE measured values instead of SAE predicted values. In order to express this rule, SAE measured values are shown by a bold solid line instead of a broken line.

In the meantime, the SAE predicted value update function 73 updates the SAE predicted value for each of the six imaging sequences (number 4 to 9) which are currently in progress or to be executed, with reference to the acquired SAE measured value. In other words, the SAE predicted value update function 73 updates the SAE predicted value of each of the imaging sequence number 4 to 9, by cumulatively adding each SAE predicted value of the imaging sequence number 4 to 9 to the SAE measured value at the time when imaging of the imaging sequence number 3 is completed. In this manner, the updated SAE predicted values of the imaging sequence number 4 to 9 are shown by, for example, a bold broken line in the graph display window W3. Incidentally, the original SAE predicted values calculated before start of imaging may be additionally illustrated by a fine broken line as reference.

The updated SAE predicted values are also reflected on display in the examination content window W1. In the example shown in FIG. 9, the SAE predicted value of the imaging sequence number 6 is increased as a result of updating based on actual values and is re-sorted from the third segment (90% or more but less than 100%) into the fourth segment (100% or more). Therefore, in the examination content window W1, display of the imaging sequence number 6 is changed into the darkest gray-scale (or red) indicative of the fourth segment.

The above-described processing of the steps ST16 to ST18 is repeated until the examination is completed. When imaging of all the imaging sequences is completed, this examination is completed (YES in the step ST19 in FIG. 3) and the above processing is also completed.

According to the above-described first embodiment, an SAE predicted value is displayed for each of the imaging sequences at the time of setting examination contents. Thus, a user can easily understand whether SAE exceeds the safety reference value in the examination or not, before start of the examination. Further, a user can easily specify the imaging protocol at which SAE is likely to exceed the safety reference value, when it is expected that SAE exceeds the safety reference value in the examination, before start of the examination. Therefore, when SAE is likely to exceed the safety reference value, a user can preliminarily take an appropriate action such as changing examination contents etc.

In addition, after the examination is started, SAE measured values calculated based on measured RF power are acquired and the SAE predicted values are sequentially updated based on the latest SAE measured value. Therefore, accuracy of SAE predicted values can be improved.

(4) Calculation and Display of SAE Predicted Value (the Second Embodiment)

As shown in FIG. 2, the magnetic resonance imaging apparatus 1 of the embodiment includes the SAE measured value storage circuit 76 (as a part of the memory circuitry 66) configured to store SAE measured values. Although the SAE measured value storage circuit 76 can be disposed in an appropriate storage device in the magnetic resonance imaging apparatus 1, the SAE measured value storage circuit 76 may be disposed in an appropriate area inside the memory circuitry 66.

In the second embodiment, the SAE predicted value calculation function 72 of the processing circuitry 60 stores SAE measured values acquired from the SAR/SAE measurement circuit 47 in the SAE measured value storage circuit 76, so that the SAE measured values to be stored are associated with patient ID (identification information of a patient).

Consider a case where a certain patient (for example, a patient A) is examined by the magnetic resonance imaging apparatus 1. In this case, a case where the examination (for example, the examination (1)) for the patient A is interrupted, then another patient is examined by the magnetic resonance imaging apparatus 1, and then the examination (1) for the patient A is resumed is possible.

Figure 10:
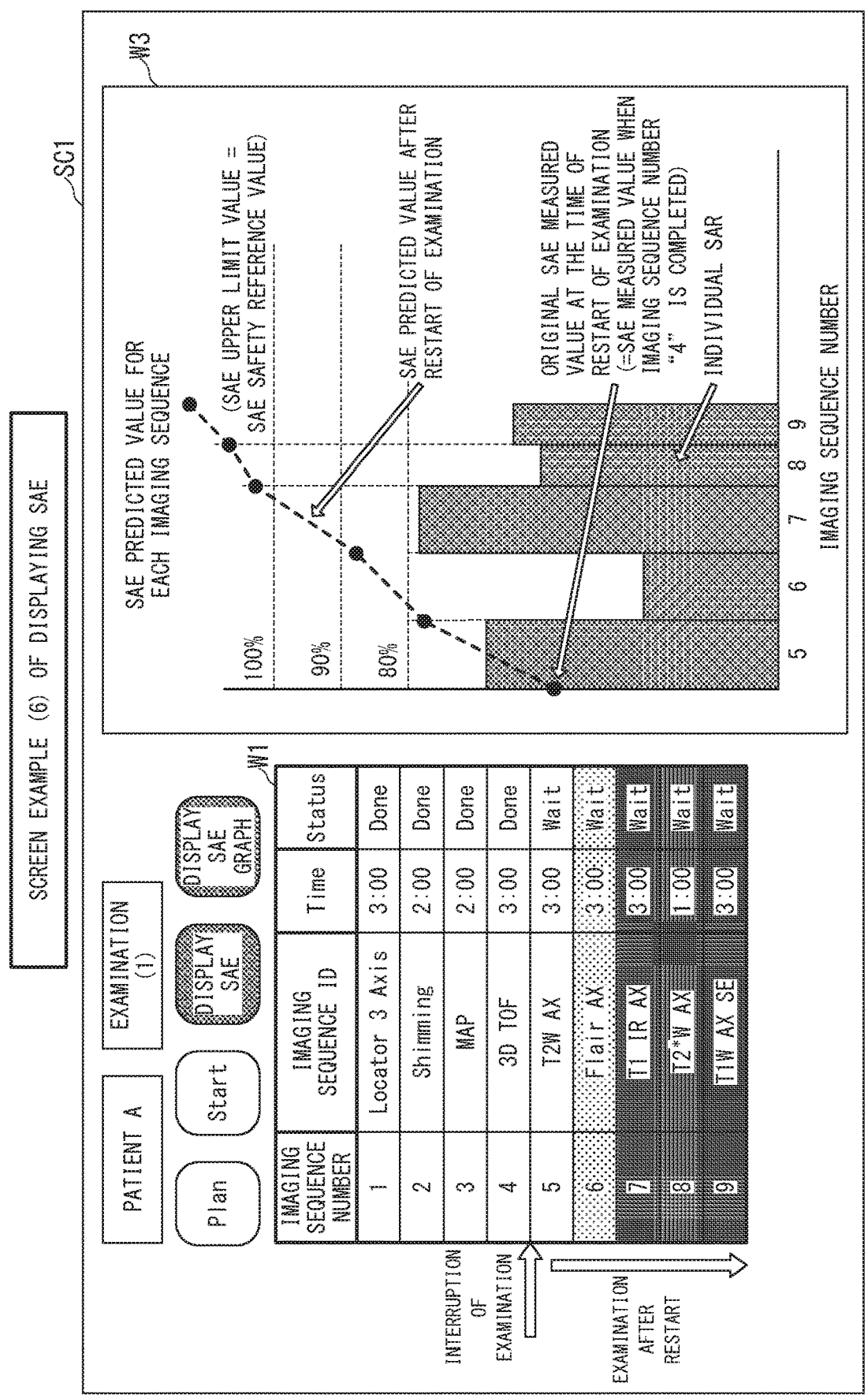
FIG. 10 is a chart showing an example of display of SAE predicted values when an examination was interrupted on the way and then the examination is restarted.

As an example in FIG. 10, a case where the examination (1) is once interrupted at the time of completing imaging of the four imaging sequences from number 1 to 4 is shown. Specifically, in the example of FIG. 10, an examination of another patient is performed to the end in this interruption period, and then imaging of the five imaging sequences from number 5 to 9 out of all the imaging sequences of the examination (1) for the patient A is resumed.

The magnetic resonance imaging apparatus 1 of the second embodiment stores SAE measured values in association with patient ID in the SAE measured value storage circuit 76 at predetermined intervals. As an example of the predetermined intervals, SAE measured values are stored each time of completing one imaging sequence. Thus, in the example shown in FIG. 10, the SAE measured value of the patient A at the time of completing imaging sequence number 4 is stored in the SAE measured value storage circuit 76.

As to resuming the examination (1) for the patient A from the imaging sequence number 5, the SAE predicted value calculation function 72 of the processing circuitry 60 reads out the SAE measured value of the patient A stored in the SAE measured value storage circuit 76. The SAE predicted value calculation function 72 calculates an SAE predicted value of each of the unexecuted imaging sequences from number 5 to 9, based on the actual value of SAE having been read out from the SAE measured value storage circuit 76.

According to the magnetic resonance imaging apparatus 1 of the second embodiment, when an examination for a patient is interrupted, the actual value of SAE for this patient at the time of interrupting the examination is stored in the SAE measured value storage circuit 76. Thereby, when the examination for this patient is resumed, SAE predicted values after resumption of the examination are calculated by using the actual value of SAE for this patient immediately before interrupting the examination stored in the SAE measured value storage circuit 76. Thus, SAE predicted values can be accurately calculated.

(5) Calculation and Display of SAE Predicted Value (the Third Embodiment)

So far, aspects of calculating SAE predicted values and displaying a relative value (such as a ratio etc.) of each SAE predicted value with respect to the SAE safety reference value in the case of executing one examination for one patient have been explained.

By contrast, a case where plural examinations are performed on one patient in a relatively short period (for example, within 24 hours) is actually possible. Similarly, a case where an examination was performed on one patient and then the same examination is performed again on the same patient in a relatively short period, for example, within 24 hours is possible.

For the above reasons, when plural different examinations are performed on the same patient in a relatively short period, the magnetic resonance imaging apparatus 1 of the third embodiment cumulatively calculates the SAE predicted value of each examination to be performed afterward based on the SAE measured value of the previously performed examination.

Similarly, when the same examination is performed again on the same patient in a relatively short period, the magnetic resonance imaging apparatus 1 of the third embodiment cumulatively calculates the SAE predicted value of the same examination to be performed afterward based on the SAE predicted value of the same examination which has been already completed. The above-described "relatively short period" means, for example, within 24 hours.

Figure 11:
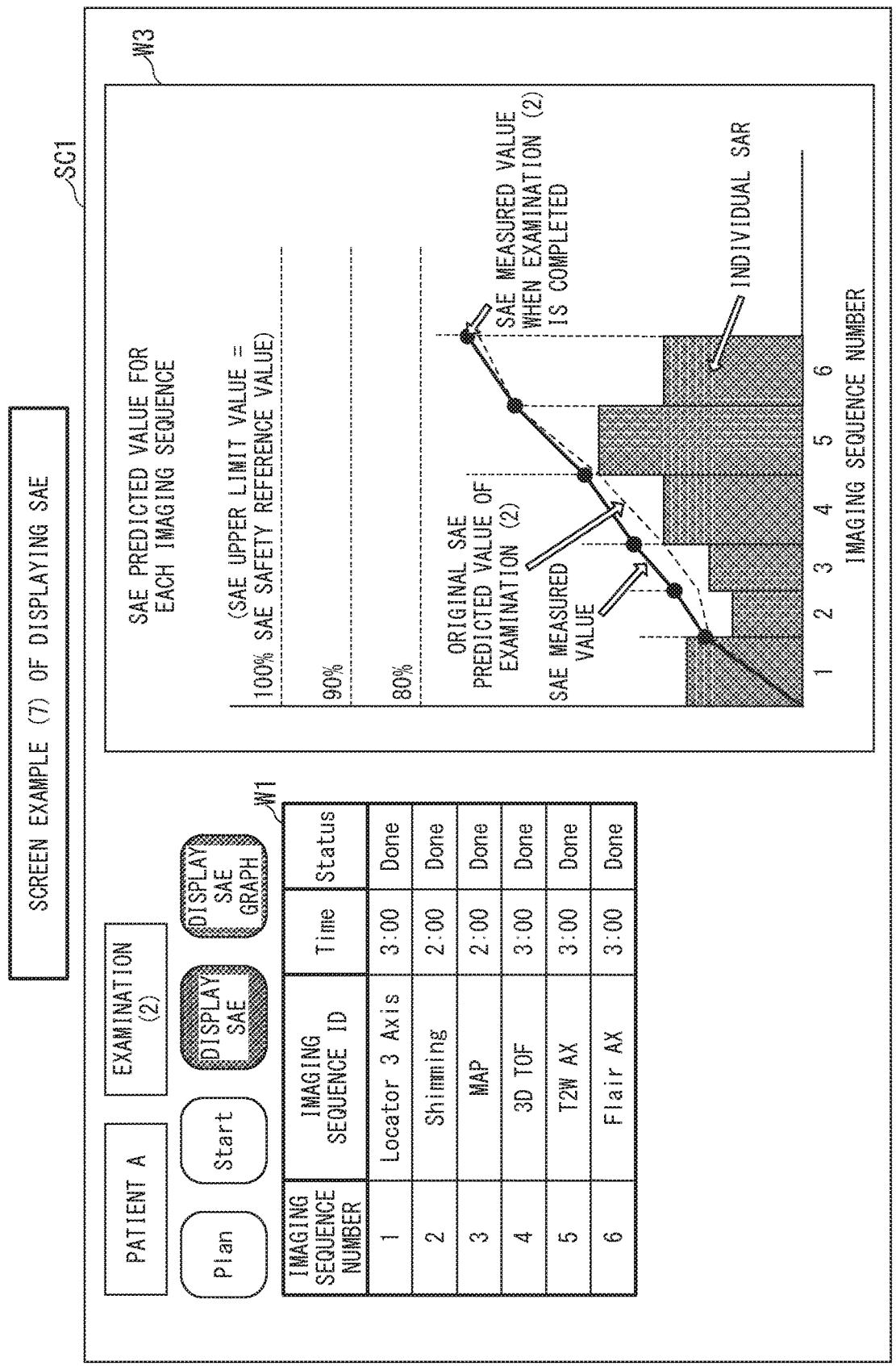
FIG. 11 is the first chart showing an example of display of SAE predicted values when plural examinations are performed on the same patient in a predetermined period.
Figure 12:
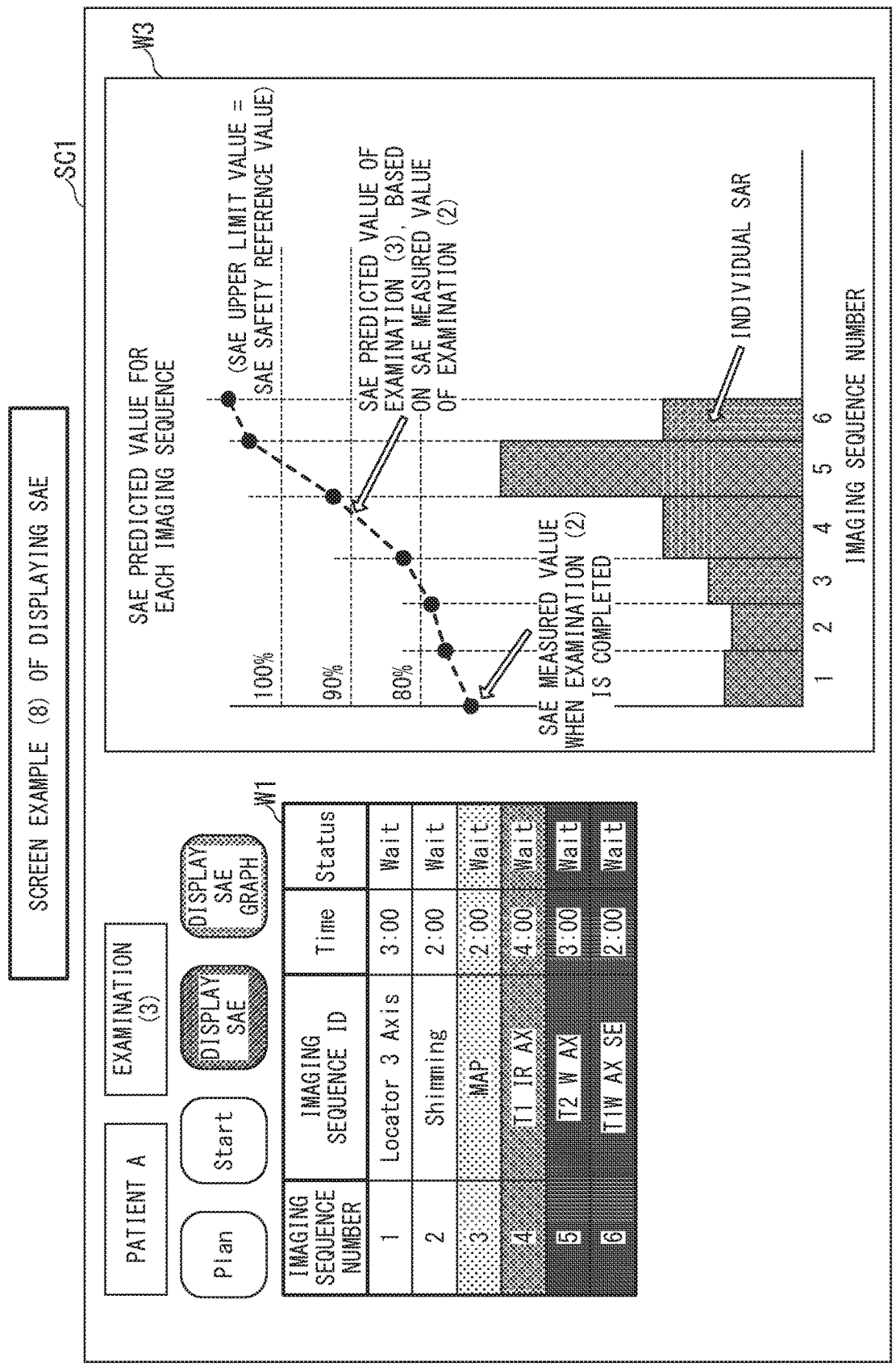
FIG. 12 is the second chart showing an example of display of SAE predicted values when plural examinations are performed on the same patient in a predetermined period.

FIG. 11 and FIG. 12 are charts explaining calculation and display of SAE predicted values performed by the above-described magnetic resonance imaging apparatus 1 of the third embodiment.

Each of FIG. 11 and FIG. 12 shows an example in which two different examinations (i.e. an examination (2) and an examination (3)) are performed on the patient A in a predetermined period (for example, within 24 hours).

FIG. 11 shows a display example at the timing when the examination (2) composed of six imaging sequences from number 1 to 6 is completed. In the graph window W3 of FIG. 11, actual values of SAE are displayed as a polygonal line graph of a bold line. In the example of FIG. 11, the SAE measured value at the time of completing the examination (2), i.e. completing the imaging sequence number 6 is also less than 80% of the SAE safety reference value.

On the other hand, FIG. 12 is a chart illustrating calculation of SAE predicted values and its display, when the examination (3) is to be performed on the patient A in a predetermined period (for example, within 24 hours) after completing the different examination (2) on the same patient A. In the third embodiment, the reference value (default value) of calculation of SAE predicted values of the examination (3) is not set to zero but it is set to the actual value of SAE at the time of completing the examination (2). In other words, the SAE predicted values of the examination (3) are calculated under the assumption that SAE of the examination (3) cumulatively increases from the actual value of SAE at the time of completing the examination (2).

When plural different examinations are performed on the same patient in a relatively short period, the magnetic resonance imaging apparatus 1 of the third embodiment calculates the SAE predicted value of each examination to be performed afterward, so that SAE of all the examinations in this short period are reflected on the SAE predicted value. Since the actual value of SAE of the examination(s) before interruption is directly reflected (without reflecting decrease of SAR during the interruption), the SAE predicted value can be calculated from the standpoint of safety side.

(6) Operation by Plural MRI Apparatuses

Figure 13:
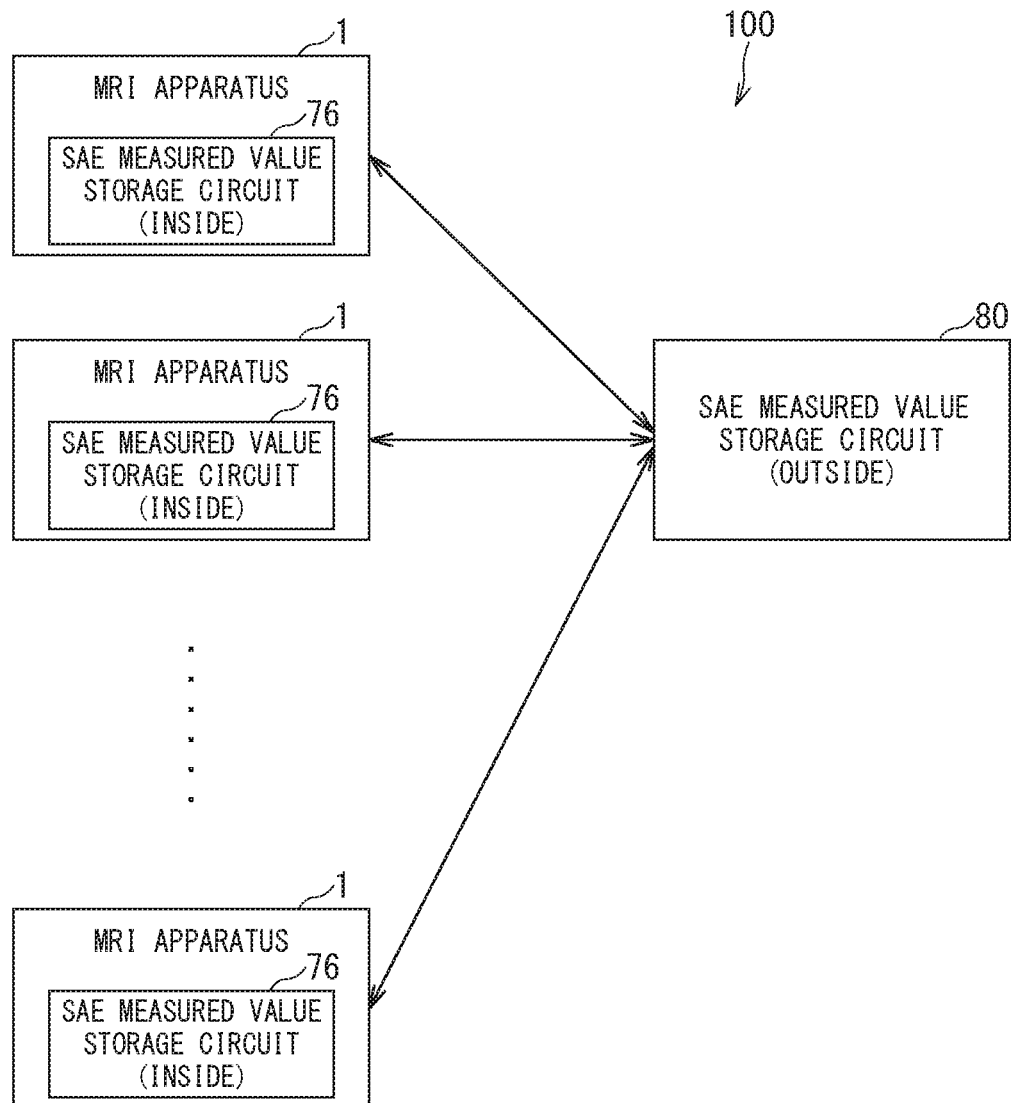
FIG. 13 is a block diagram showing an example of configuration of a system including plural magnetic resonance imaging apparatuses.

FIG. 13 is a block diagram showing an example of configuration of an MRI (magnetic resonance imaging) network system 100 in which each of plural magnetic resonance imaging apparatuses 1 is connected to an external SAE measured value storage circuit 80.

Large hospitals are equipped with plural magnetic resonance imaging apparatuses, in many cases. When an examination is interrupted on the way and this examination is resumed from the interrupted part (like the operation form in the above-described second embodiment) in such large hospitals, the following case is possible. That is, the magnetic resonance imaging apparatus 1 used for the examination before the interruption is different from the magnetic resonance imaging apparatus 1 to be used for the rest of the examination after the resumption.

In addition, when at least two different examination are performed on the same patient in a relatively short period (like the operation form in the above-described third embodiment), the following case is possible. That is, the magnetic resonance imaging apparatus 1 different from the one used for one examination is used for another examination, depending on the examinations.

The MRI network system 100 shown in FIG. 13 stores SAE measured values acquired in the examination before interruption and/or SAE measured values acquired in an previously executed examination not only in the SAE measured value storage circuit 76 inside the magnetic resonance imaging apparatus 1 but also in the SAE measured value storage circuit 80 outside the magnetic resonance imaging apparatus 1. The MRI network system 100 performs the processing of storing SAE measured values, in such a manner that ID of each patient is correlated to the SAE measured value obtained from this patient.

As a result, even if the magnetic resonance imaging apparatus 1 used for the (unexecuted) examination after resumption is different from the one used for the executed examination, the SAE measured value at the time of interrupting the examination can be acquired from the external SAE measured value storage circuit 80. Similarly, even if the magnetic resonance imaging apparatus 1 used for the examination to be performed afterward is different from the one used for the executed examination, the SAE measured value of the same patient in the previously executed examination can be acquired from the external SAE measured value storage circuit 80. Therefore, SAE predicted values after resumption of the examination and/or SAE predicted values for the examination to be performed afterward can be accurately calculated.

As a supplementary note, the term "processor" used for explaining the processing circuitry 60 etc. means, for Instance, a circuit such as a CPU (Central Processing Unit), a GPU (Graphics Processing Unit), an ASIC (Application Specific Integrated Circuit), a programmable logic device including an SPLD (Simple Programmable Logic Device) and a CPLD (Complex Programmable Logic Device) as examples, an FPGA (Field Programmable Gate Array), and so on.

The number of processors provided for the processing circuitry 60 may be one, two, or more.

The processor of the processing circuitry 60 implements each function by reading out a program directly stored in its own circuit and executing the program. In addition, the programs executed by the processor of the processing circuitry 60 may be stored in a non-illustrated memory provided in the processing circuitry 60, instead of storing those programs in the processors.

When plural of processors are included in the processing circuitry 60, a memory for storing the programs may be provided for each processor. In addition, a single memory may collectively store the programs corresponding to the functions of all the processors, when plural processors are included in the processing circuitry 60.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) system comprising:
   at least one MRI gantry configured to execute a patient examination including consecutive execution of plural MRI sequences, which MRI sequences each include application of radio frequency (RF) energy to the examined patient and which consecutive executions of MRI sequences can be interrupted after one of the MRI sequences and later resumed with the next remaining of the plural MRI sequences to complete an examination;
   at least one processor coupled to a memory circuit and a display device, the at least one processor being coupled to acquire a measure related to RF power applied to the patient and store in the memory circuit an actual measured value of specific absorption energy (SAE) during an examination, the actual measured value of SAE being calculated based on the acquired measure related to RF power;
   the at least one processor being configured to:
   calculate an SAE value for the next remaining of the plural MRI sequences, which is related to a resumed examination, based on a stored actual measured SAE value which existed when the examination was interrupted and stored in the memory circuit, and
   cause the display device to display a relationship between an upper limit of SAE value and the calculated SAE value related to the resumed examination.

2. The magnetic resonance imaging apparatus according to claim 1, wherein the at least one processor is further configured to
   calculate the SAE value related to the resumed examination for each of the plural MRI sequences; and
   cause the display to display information on the calculated SAE value for each of the plural MRI sequences.

3. The magnetic resonance imaging apparatus according to claim 2, wherein the at least one processor is further configured to cause the display to
   (a) display an identification of each of the plural MRI sequences by arranging the plural MRI sequences in execution order, and
   (b) additionally display the information on the calculated SAE value, in parallel with display of the identification of each of the plural MRI sequences.

4. The magnetic resonance imaging apparatus according to claim 3, wherein the at least one processor is further configured to cause the display to
   (a) display a ratio of the calculated SAE value to the upper limit of SAE value, as the information on the calculated SAE value, and
   (b) change a display aspect of the identification of each of the plural MRI sequences, depending on the ratio of the calculated SAE value to the upper limit of SAE value.

5. The magnetic resonance imaging apparatus according to claim 4, wherein the at least one processor is further configured to cause the display to display the aspect of the identification of each of the plural MRI sequences, by changing chromatic color or gray-scale depending on the ratio of the calculated SAE value to the upper limit of SAE value.

6. The magnetic resonance imaging apparatus according to claim 4, wherein the at least one processor is further configured to cause the display to display an icon adjacent to the identification of each of the plural MRI sequences, by changing an aspect of the icon depending on the ratio of the calculated SAE value to the upper limit of SAE value.

7. The magnetic resonance imaging apparatus according to claim 1, wherein the at least one processor is further configured to cause the display to display a graph indicating relation between the calculated SAE value and the upper limit of SAE value.

8. A magnetic resonance imaging (MRI) support method comprising:
   receiving actual measured value of specific absorption energy (SAE), which SAE is based on radio frequency (RF) power applied to a patient while executing a patient examination including consecutive execution of plural MRI sequences, which MRI sequences each include application of RF energy to the examined patient and which consecutive executions of MRI sequences can be interrupted after one of the MRI sequences and later resumed with the next remaining of the plural MRI sequences to complete an examination;
   storing an actual measured SAE value in accordance with completion of a MRI sequence;
   calculating a SAE value for the next remaining of the plural MRI sequences, which is related to a resumed examination, based on a stored actual measured SAE value which existed when the examination was interrupted, and
   displaying a relationship between an upper limit of SAE value and the calculated SAE value related to the resumed examination.

9. A magnetic resonance imaging (MRI) support method comprising:
   calculating actual measured value of specific absorption energy (SAE), based on radio frequency (RF) power applied to a patient while executing a patient examination including consecutive execution of plural MRI sequences, which MRI sequences each include application of RF energy to the examined patient and which consecutive executions of MRI sequences can be interrupted after one of the MRI sequences and later resumed with the next remaining of the plural MRI sequences to complete an examination;
   storing an actual measured SAE value in accordance with completion of a MRI sequence;
   calculating a SAE value for the next remaining of the plural MRI sequences, which is related to a resumed examination, based on a stored actual measured SAE value which existed when the examination was interrupted, and
   displaying a relationship between an upper limit of SAE value and the calculated SAE value related to the resumed examination.

* * * * *